United States Patent
Esping Östlin et al.

(10) Patent No.: US 9,597,236 B2
(45) Date of Patent: Mar. 21, 2017

(54) ABSORBENT CORE EXHIBITING CONTROLLED DEFORMATION IN USE AND ABSORBENT ARTICLE COMPRISING SAID CORE

(71) Applicant: SCA Hygiene Products AB, Gothenburg (SE)

(72) Inventors: Hanna Esping Östlin, Pixbo (SE); Edward Guidotti, Gothenburg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 14/646,196

(22) PCT Filed: Dec. 27, 2012

(86) PCT No.: PCT/SE2012/051499
§ 371 (c)(1),
(2) Date: May 20, 2015

(87) PCT Pub. No.: WO2014/104952
PCT Pub. Date: Jul. 3, 2014

(65) Prior Publication Data
US 2015/0328063 A1    Nov. 19, 2015

(51) Int. Cl.
A61F 13/536    (2006.01)
A61F 13/539    (2006.01)
(Continued)

(52) U.S. Cl.
CPC .......... *A61F 13/539* (2013.01); *A61F 13/533* (2013.01); *A61F 13/535* (2013.01);
(Continued)

(58) Field of Classification Search
CPC .............. A61F 13/4704; A61F 13/4756; A61F 13/49001; A61F 13/533; A61F 13/534;
(Continued)

(56) References Cited

U.S. PATENT DOCUMENTS 4,762,521 A    8/1988   Roessler et al.
4,988,344 A *   1/1991   Reising ................. A61F 13/535
                                                      604/358
(Continued)

FOREIGN PATENT DOCUMENTS

EP    1 723 939 A1    11/2006
EP    2 298 258 A1    3/2011
(Continued)

OTHER PUBLICATIONS

International Search Report (PCT/ISA/210) mailed on Sep. 20, 2013, by the Swedish Patent Office as the International Searching Authority for International Application No. PCT/SE2012/051499.
(Continued)

*Primary Examiner* — Lynne Anderson
(74) *Attorney, Agent, or Firm* — Buchanan Ingersoll & Rooney PC

(57) ABSTRACT

An absorption body intended to form part of an absorbent disposable article includes a first absorption layer intended to face towards the user upon use and a second absorption layer intended to face away from the user upon use. The first absorption layer has a longitudinal opening in the crotch area and the second absorption layer has a longitudinal compression arranged in the crotch area.

18 Claims, 11 Drawing Sheets

(51) Int. Cl.
*A61F 13/533* (2006.01)
*A61F 13/53* (2006.01)
*A61F 13/47* (2006.01)
*A61F 13/534* (2006.01)
*A61F 13/49* (2006.01)
*A61F 13/15* (2006.01)
*A61F 13/535* (2006.01)

(52) U.S. Cl.
CPC ........ *A61F 13/536* (2013.01); *A61F 13/4704* (2013.01); *A61F 13/49001* (2013.01); *A61F 2013/15406* (2013.01); *A61F 2013/5355* (2013.01); *A61F 2013/53445* (2013.01); *A61F 2013/530481* (2013.01); *A61F 2013/530963* (2013.01); *A61F 2013/530985* (2013.01)

(58) Field of Classification Search
CPC ................. A61F 13/535; A61F 13/536; A61F 2013/15406; A61F 2013/53445; A61F 2013/5355
USPC .................................................. 604/385.101
See application file for complete search history.

(56) References Cited

U.S. PATENT DOCUMENTS

| | | | |
|---|---|---|---|
| 5,197,959 A | 3/1993 | Buell | |
| 5,728,084 A | 3/1998 | Palumbo et al. | |
| 5,795,344 A * | 8/1998 | Chappell | A61F 13/533 604/379 |
| 5,810,798 A * | 9/1998 | Finch | A61F 13/535 428/172 |
| 8,764,719 B2 * | 7/2014 | Bissah | A61F 13/4756 604/385.01 |
| 9,066,837 B2 * | 6/2015 | Kim | A61F 13/4756 |
| 9,259,361 B2 * | 2/2016 | Johansson | A61F 13/4751 |
| 2002/0052587 A1 * | 5/2002 | Magnusson | A61F 13/4756 604/378 |
| 2006/0069371 A1 | 3/2006 | Ohashi et al. | |
| 2009/0112175 A1 * | 4/2009 | Bissah | A61F 13/535 604/385.101 |
| 2012/0220972 A1 | 8/2012 | Kawamura et al. | |
| 2012/0289923 A1 | 11/2012 | Watabe et al. | |
| 2014/0249497 A1 | 9/2014 | Bissah et al. | |
| 2015/0119842 A1 * | 4/2015 | Kosaka | A61F 13/4752 604/385.101 |

FOREIGN PATENT DOCUMENTS

| | | |
|---|---|---|
| EP | 2 612 636 A1 | 7/2013 |
| EP | 2 659 872 A1 | 11/2013 |
| GB | 2296437 A | 7/1996 |
| JP | 2002-513043 A | 5/2002 |
| JP | 2007-097954 A | 4/2007 |
| JP | 2008-173247 A | 7/2008 |
| JP | 2008-284190 A | 11/2008 |
| JP | 2011-518613 A | 6/2011 |
| JP | 2012-016435 A | 1/2012 |
| RU | 2192835 | 11/2002 |
| RU | 2010136918 | 3/2012 |
| WO | 99/55393 A1 | 11/1999 |
| WO | 2009/134626 A1 | 11/2009 |
| WO | WO 2011/105108 A1 | 9/2011 |
| WO | WO 2012/005249 A1 | 1/2012 |
| WO | WO 2012/086210 A1 | 6/2012 |
| WO | WO 2012/086487 A1 | 6/2012 |
| WO | WO 2014/104952 A1 | 7/2014 |

OTHER PUBLICATIONS

Written Opinion (PCT/ISA/237) mailed on Sep. 20, 2013, by the Swedish Patent Office as the International Searching Authority for International Application No. PCT/SE2012/051499.

International Preliminary Report on Patentability (PCT/IPEA/409) mailed on Mar. 23, 2015, by the Swedish Patent Office as the International Preliminary Examining Authority for International Application No. PCT/SE2012/051499.

Notice of Reasons for Rejection dated Jun. 6, 2016, issues in the corresponding Japanese Patent Application No. 2015-550357 and English translation (7 pages).

Official Action issued in corresponding Russian Patent Application No. 2015130909/20(047613), dated Nov. 11, 2016; with English Translation (12 pages).

* cited by examiner

ABSORBENT CORE EXHIBITING CONTROLLED DEFORMATION IN USE AND ABSORBENT ARTICLE COMPRISING SAID CORE

TECHNICAL FIELD

The present disclosure relates to an absorption body intended to form part of a disposable absorbent article. The absorption body has a longitudinal centre line, a crotch area, a front end area and a rear end area.

The absorption body further comprises a first absorption layer intended to face towards the user upon use and having longitudinal edges, and a second absorption layer intended to face away from the user upon use and having longitudinal edges. The first absorption layer has a first longitudinal opening arranged in the crotch area and the second absorption layer has a first longitudinal compression arranged in the crotch area.

BACKGROUND

It is known that absorption bodies intended to form part of absorbent articles should have a sufficient absorption capacity and a capability to take up rapidly escaping liquid when for example an incontinent adult wearer of the article empties their entire bladder in an uncontrolled manner.

Depending on what the absorbent article is intended for, the absorption capacity varies within wide boundaries, for example, a capacity of 4 grams is sufficient for the smallest size of a sanitary towel, while a capacity of over 1000 grams is required for the largest articles intended for incontinent adults.

To manufacture articles with sufficient absorption capacity is not a big problem today when there are gel-forming, highly absorbent particles, so-called superabsorbents, to mix in in the absorption bodies of the absorbent articles.

One type of problem with today's very thin and hard compressed articles is to ensure that the articles can take up liquid that is secreted and impacts on the article at a high flow rate. For example, absorbent articles for incontinent adult wearers should be able to take up several hundred ml of urine excreted in 10 seconds. If the absorbent article's absorption body is incapable of taking up and absorbing this large flow, there is a major risk that the urine runs on the surface of the article and out over the edge of this.

One solution to the problem of taking up rapidly secreted bodily fluid is to arrange special material layers between the absorption body and the user that are intended to take up and temporarily store fluid while waiting for the absorption body to manage to absorb the fluid. Examples of such materials are resilient pads of polyester fibres, for example.

Another frequent solution is to create from today's thin, wide crotch structure a bowl-shaped structure between the wearer's thighs in which the fluid can temporarily be collected before it penetrates the absorption body. The articles' absorption bodies have been provided in this case with compressions, slits, contracting elastic elements or the like to control the shape of the articles when they are pressed together between the wearer's thighs in use.

In patent application GB 2,296,437 (Hansson et al Mölnlycke AB) it is described how the shaping of an absorbent article can be controlled when it is exposed to forces substantially perpendicular to the longitudinal direction of the article.

The article comprises an absorbent layer that has a through slit and a first material layer over one surface of the absorbent layer, and a second material layer over the opposing surface of the absorbent layer. One material layer is joined to the absorbent layer up to said slit, while the second material layer is not joined up to said slit. When the article is exposed to compressive forces directed perpendicularly to the slit, the article bends/is folded forcibly in the direction away from the unjoined side of the absorption layer.

In patent document WO 2011/105108 A1 (Mukai et al, Uni-Charm), a refined variant is described of an absorption body that is shaped between the user's thighs when the article is used.

The absorption body in WO 2011/105108 A1 consists of 2 layers, wherein the layer that is arranged away from the user has a longitudinal opening arranged centrally in the crotch part along the longitudinal centre line. The second absorption layer that is oriented nearest to the wearer of the article has side openings placed symmetrically between the longitudinal centre line of the layer and its respective longitudinal edge.

The document shows that the design of the absorption body with longitudinal openings in both absorption layers means that the absorbent article is shaped like a W in the crotch area when it is pressed together between a user's thighs.

It has proved to be the case, however, that, regardless of whether the article is designed to assume a simple bowl shape, a U- or V-shape, or a more sophisticated bowl shape, a W-shape, upon use, it is a problem that the article does not assume the intended shape when it is placed on a user.

It is not unusual, for example, for the article to assume an inverted shape when it is exposed to pressure forces from the user's thighs, meaning for example that the U-shape instead becomes an inverted U-shape ((∩-shape) and the W-shape becomes an inverted W-shape (M-shape).

It has also proved to be the case that articles intended to assume a U-shape, a V-shape or a W-shape when they are deformed in a transverse direction between the user's thighs have a rebound force against the user's thighs that is much too low, wherein the article is not able to effectively seal against the thighs when in use.

There is thus a need for improved absorbent articles that shape themselves in a desired manner with greater reliability when the article is placed and pressed together between a user's thighs. The requirement exists regardless of whether it is a question of absorbent articles intended for children or adults with urinary incontinence.

Furthermore, there is a need for an article which, in the deformed state according to the above, has an increased rebound force in a transverse direction against the user's thighs when in use.

SUMMARY

With the present disclosure, however, an absorption body of the type discussed at the beginning has been achieved that substantially removes the problems in connection with previously known absorption bodies.

An absorption body according to the present disclosure is distinguished primarily in that the first longitudinal opening and the first longitudinal compression substantially overlap one another.

The arrangement with an absorption body comprising a longitudinal opening and a longitudinal compression that overlap one another means that an absorbent article that comprises an absorption body according to the present disclosure is deformed in a certain way when it is pressed together between the user's legs.

According to one aspect of the present disclosure, the first longitudinal opening of the first absorption layer and the first longitudinal compression of the second absorption layer coincide substantially with the longitudinal centre line.

By centring the opening and the compression, a centred V-shape is formed when an article comprising the absorption body is pressed together between a user's thighs.

According to another aspect of the present disclosure, the first absorption layer has a second longitudinal opening arranged in the crotch area between the longitudinal centre line of the absorption layer and one longitudinal edge, the first longitudinal opening being arranged between the longitudinal centre line and the opposing longitudinal edge.

The second absorption layer further has a second longitudinal compression arranged in the crotch area between the longitudinal centre line and one longitudinal edge of the absorption layer, the first longitudinal compression being arranged between the longitudinal centre line and the opposing longitudinal edge.

The second longitudinal opening and the second longitudinal compression substantially overlap one another in this case in the same way as the first longitudinal opening and the first longitudinal compression substantially overlap one another.

By arranging the overlapping openings and compressions on each side of the centre line a symmetrical U-shape is formed when an article comprising the is absorption body is pressed together between a user's thighs.

According to a further aspect of the present disclosure, the first absorption layer has a third longitudinal compression arranged in the crotch area substantially coinciding with the longitudinal centre line, and the second absorption layer has a third longitudinal opening arranged in the crotch area substantially coinciding with the longitudinal centre line. The third longitudinal compression and the third longitudinal opening overlap one another here.

A symmetrical W-shape is created when an article comprising the absorption body is pressed together between a user's thighs.

According to an aspect of the present disclosure, the absorption body comprises an acquisition material that is arranged on the side of the first absorption layer that is intended to face towards the user.

A special acquisition material in accordance with the present disclosure takes up rapidly incoming fluid and temporarily stores the fluid before adjacent absorption layers are able to take up the fluid.

According to an aspect of the present disclosure, the acquisition material is divided into 2 separate parts. One part is arranged between the longitudinal centre line and one longitudinal edge and the other part is arranged between the longitudinal centre line and the other longitudinal edge.

The respective part of the acquisition material is at a distance from the longitudinal centre line and from its adjacent longitudinal edge.

A two-piece acquisition material is particularly advantageous when the absorbent article is fully folded together about its longitudinal centre line when in use, i.e. when one half of the absorbent article rests against the opposing longitudinal half of the article.

According to an aspect of the present disclosure, the first and second absorption layer have substantially the same surface weights, wherein the respective absorption layer's surface weight can vary from 50 g/m$^2$ to 1000 g/m$^2$.

According to another aspect, the respective absorption layer can have a content of highly absorbent polymer material, so-called SAP, of between 0% and 80%.

One absorption layer has, according to one aspect of the present disclosure, a greater extension in the longitudinal direction than the second absorption layer and according to a another aspect, the front end area and rear end area of the absorption body have a greater extension in the transverse direction than the crotch area.

According to one aspect, the disposable article containing an absorption body in accordance with the present disclosure consists of a baby's nappy and according to another aspect of an incontinence pad for incontinent adult users.

According to one aspect of the present disclosure, the absorbent disposable article comprises a liquid-permeable envelope layer that has hydrophilic properties. The hydrophilic properties are in this case at least arranged in longitudinal zones overlapping the longitudinal edges of the absorption body.

DESCRIPTION OF EMBODIMENTS

Figure 1:
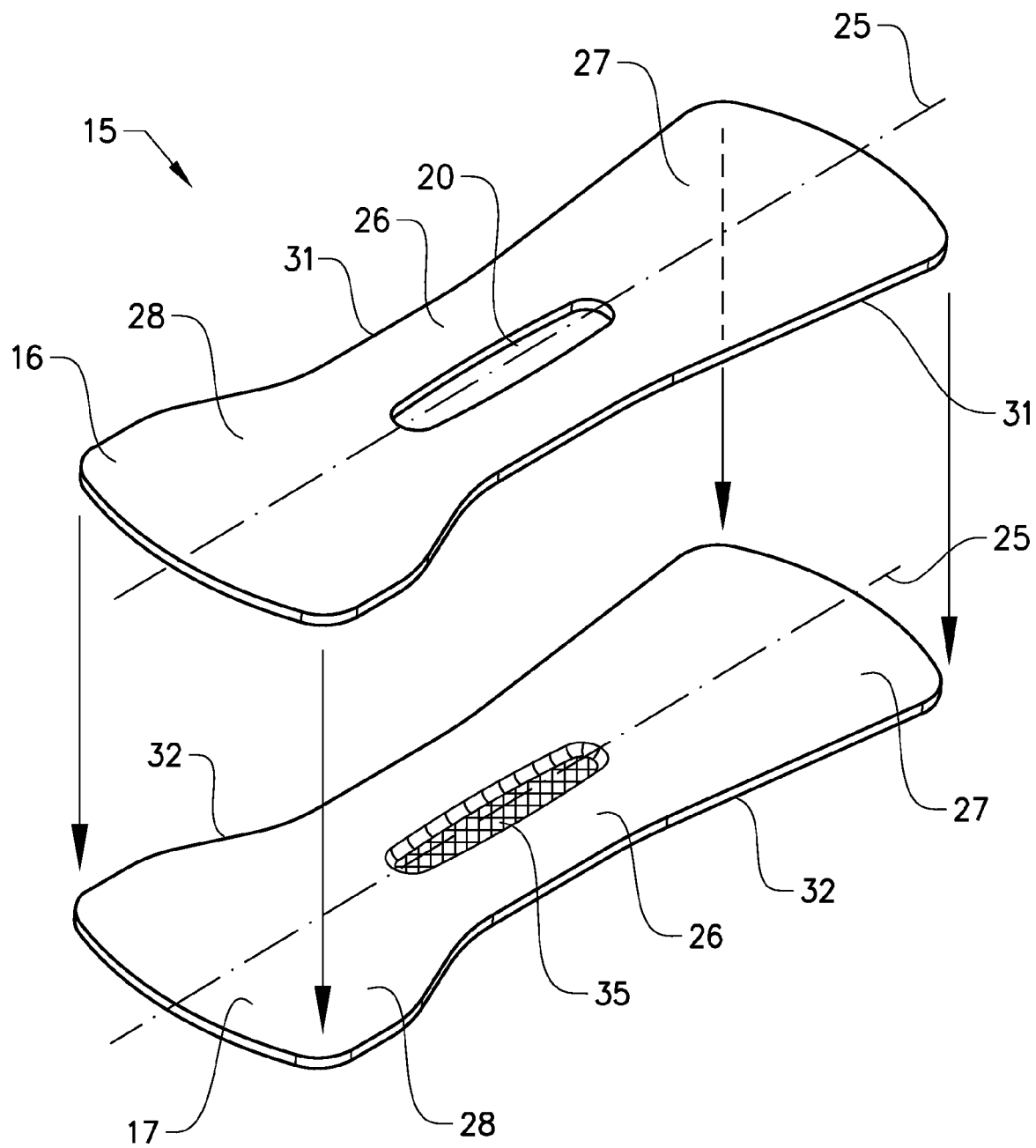
FIG. 1 shows a drawing in perspective of an absorption body in accordance with a first aspect of the present disclosure, in which the two absorption layers of the absorption body are shown separated from one another for greater clarity.

The present disclosure relates to an absorption body intended to form part of an absorbent article. The absorption body comprises at least two absorption layers, wherein one absorption layer is oriented towards the user upon use and the other absorption layer is oriented away from the user upon use.

At least the absorption layer arranged towards the user has at least one longitudinal opening and the absorption layer arranged away from the user has at least one longitudinal compression.

The two absorption layers are arranged in such a way that openings and compressions of the two absorption layers cooperate so that the absorption article comprising the absorption body is shaped in a desired manner when it is placed on a user and pressed together transversely between the latter's legs.

A first aspect of the present disclosure relates to an absorption body that, incorporated into an absorbent article, assumes a bowl shape (U-shape) when the article is pressed together transversely between a user's thighs.

The present disclosure also relates to absorbent articles comprising absorption bodies that are shaped according to the above. A plurality of types of absorbent articles is meant in this case by absorbent articles, such as, for is example, all-in-one diapers, pant diapers, belt diapers or sanitary napkins.

So-called all-in-one diapers are characterised in that they include fastening tabs with which the front and rear waist part of the diaper are joined when the diaper is applied around the waist of a user. All-in-one diapers usually comprise elastic areas by the leg cut-outs and in connection with the waist area, where at least parts of the waist section usually comprise elastic elements. The fastening tabs comprise elastic areas on some all-in-one diapers. Furthermore, the fastening tabs can comprise adhesive surfaces that are connected to surfaces on the opposing end region to which the adhesive sticks. Hook and loop type fastening systems are a common occurrence today.

So-called pant diapers are characterised primarily in that they have already been folded during manufacture about a substantially transverse fold line in the crotch part of the pant diapers, and thereafter joined at the waist. This type of diaper is intended to be put on a user precisely like a pair of underpants, i.e. drawn over the user's legs. The joining at the waist part of the pant diapers can usually be broken open, wherein the pant diapers can be removed following use without them having to be pulled down over the user's feet when they are to be removed. This option is especially appreciated when the pant diapers are smeared with faeces after use. Pant diapers normally comprise both elastic areas in the waist section and around the leg openings.

Pant diapers that can be opened and reclosed also exist. Such pant diapers are supplied folded together at the waist, but can be opened to check the contents of the article, for example, and then reclosed afterwards.

Belt diapers are characterised in that they comprise a belt that is transverse oriented in relation to the absorbent part of the diaper and connected to either the front or rear transverse edge of the nappy.

When putting on such a belt diaper, the belt is fixed, in a first stage, around the user's waist. The absorbent part of the belt is hanging loose from the belt in this case. The absorbent part of the nappy is then led between the user's legs and fastened to the belt, wherein the belt comprises fixing surfaces intended to stick to the fixing element arranged on the absorbent part of the nappy by its free transverse edge. The belt and the leg openings are usually elasticated on belt nappies.

Another type of belt diaper is in two pieces and consists of a separate belt and a separate absorbent structure. When in use the belt is fastened around the user's waist, following which the absorbent structure is joined to the outside of the belt by means of hook and loop elements or tape elements in the corners of the absorption structure.

All-in-one diapers, pant diapers or belt diapers can consist of baby diapers intended for children who are not yet potty-trained or of incontinence protection intended for incontinent adult users.

Figure 2A:
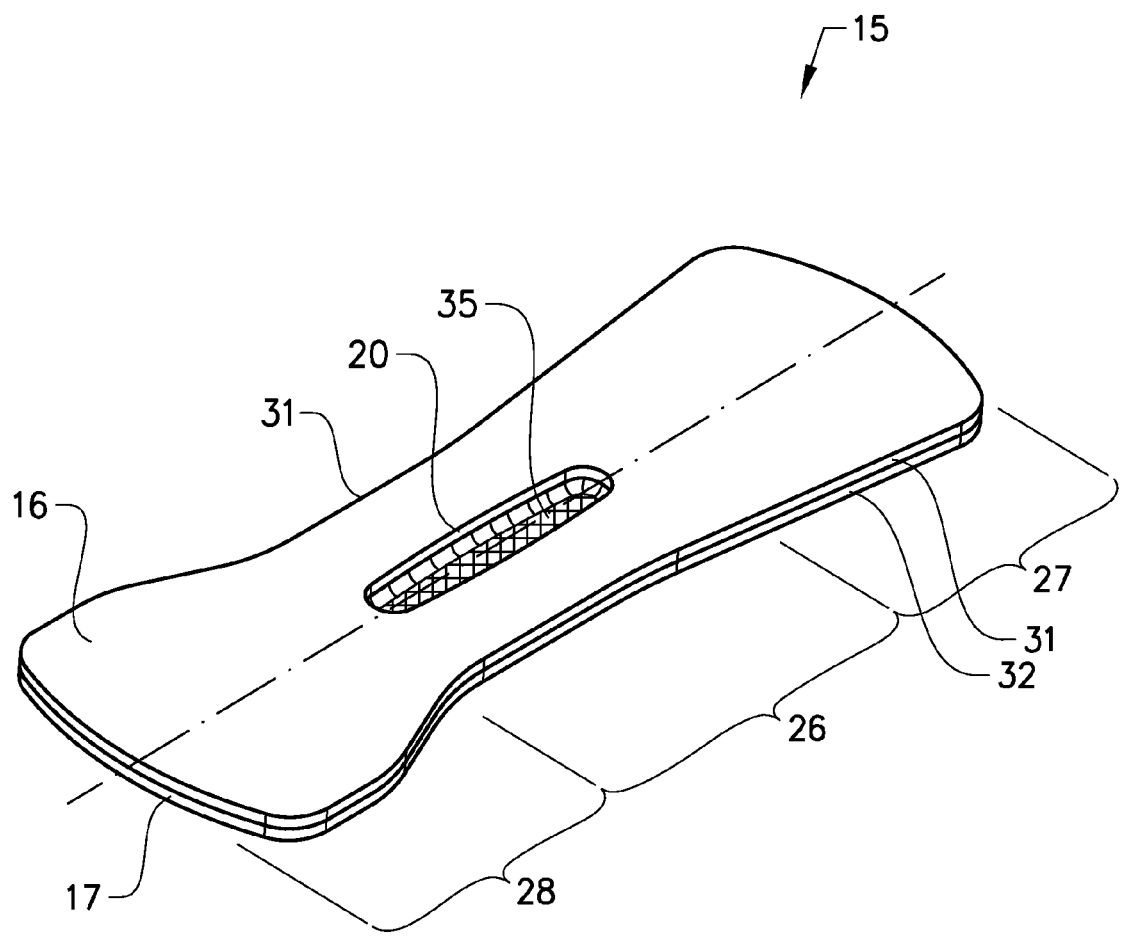
FIG. 2a shows the absorption body in FIG. 1 when the two absorption layers of the absorption body are arranged on one another.

FIGS. 1 and 2 show an absorption body 15 in accordance with a first aspect of the present disclosure. The absorption body 15 comprises a first absorption layer 16 and a second absorption layer 17 comprising cellulose fluff pulp among other things.

In FIG. 1, the first and second absorption layers 16, 17 of the absorption body 15 have been separated from one another to increase the clarity, while FIG. 2 shows an absorption body 15 as it is arranged when it is applied in an absorbent article.

Alternatively, the absorption body 15 can comprise further absorption layers. The cellulose fluff pulp in many absorption bodies is mixed with fibres or particles of a highly absorbent polymer material of the type that chemically binds large quantities of fluid on absorption with the formation of a fluid-holding gel.

The respective absorption layers 16, 17 can have a surface weight from 50 is $g/m^2$ up to 1000 $g/m^2$ and can contain 0-80% of highly absorbent polymer material, so-called SAP.

Components for improving various properties of the absorption body 15 can also form part of the absorption body 15. Examples of such components are binding fibres, various types of fluid-dispersing layers or fibres, dimensionally stabilising components, reinforcing fibres or the like. Such components are not shown in any of the figures.

The absorption layers 16, 17 are usually produced in line in the same machine that produces the entire absorbent article, but it is also the case that the absorption layers 16, 17 are produced from prefabricated absorption material. Prefabricated absorption material is usually supplied in roll form, the material being cut and folded to the prescribed configuration. Prefabricated absorption material can contain the same components as absorption bodies manufactured in line. Binding fibres are generally an important component in prefabricated absorption materials for these to hold together during handling.

The absorption body 15 has a front end area 27, a rear end area 28 and a crotch area 26 arranged between the end areas 27, 28. The absorption body 15 has an hourglass shape, the crotch area 26 being narrower than the front and the rear end area 27, 28.

Alternatively, the absorption body 15 can have another shape, for example are substantially rectangular absorption bodies common. The absorption body 15 has a longitudinal centre line 25.

The first absorption layer 16 has longitudinal edges 31.

In the crotch area 26 of the first absorption layer 16, coinciding with the centre line 25, a longitudinal opening 20 is arranged. The opening 20 has its main extension in the crotch area 26, but can also extend into both the front and rear end area 27, 28. The opening 20 extends 30% of the length of the first absorption layer 16 in a longitudinal direction.

In alternative aspects of the present disclosure, the opening 20 can have an extension in a longitudinal direction of between 10% and 100% of the length of the first absorption layer 16.

The opening 20 has a width perpendicular to the longitudinal direction of 15 mm but can vary in alternative aspects of the present disclosure between 2 and 30 mm, preferably between 5 and 20 mm and even more preferably between 8 and 15 mm.

The second absorption layer 17 has longitudinal edges 32. In the crotch area 26 of the second absorption layer 17, coinciding with the centre line 25, a longitudinal compression 35 is arranged. The compression 35 is here, in relation to surrounding parts of the absorption layer 17, clearly visible. The thickness of the absorption layer 17 has been reduced by 20-90% in the central parts of the compression 17, preferably by 50-90% and even more preferably by 70-90%.

The compression 35 has its main extension in a longitudinal direction in the crotch area 26, but can also extend into both the front and rear end area 27, 28.

The compression 35 extends 30% of the length of the second absorption layer 17 in a longitudinal direction, meaning that the compression 35 extends as far as the opening 20 in the first absorption layer 16.

In alternative aspects of the present disclosure, the compression 35 can have an extension in a longitudinal direction from 30% of the length of the opening 20 of the first absorption layer 16 up to the whole length of the second absorption layer 17. The compression 35 has a width perpendicular to the longitudinal direction of 15 mm but in alternative aspects of the present disclosure can have a width of between 2 and 30 mm, preferably between 5 and 20 mm and even more preferably between 8 and 15 mm.

The absorption body 15 is distinguished primarily in that the opening 20 is arranged in the first absorption layer 16 and the compression 35 arranged in the second absorption layer 17 substantially overlap one another. Tests have shown that by letting the longitudinal opening of one layer and the longitudinal compression of the other layer overlap one another, the article comprising the absorption body is shaped with substantially greater reliability in the desired manner when it is exposed to forces perpendicular to the longitudinal direction. Furthermore, an improved rebound force perpendicular to the longitudinal direction is obtained, which effectively seals against the user's thighs, whereby many leakages are avoided.

The crotch area 26 of the absorption body 15 is shaped, when it is exposed to forces substantially perpendicular to the longitudinal centre line 25, substantially like a V with the second absorption layer 17, comprising the compression 35, oriented on the outside of the V-shape and the first absorption layer 16, comprising the opening 20, oriented inwards in the V-shape.

The compression 35 in the second absorption layer 17 functions like a fold notch when the absorption body 15 is shaped. The width of the opening 20 of the first absorption layer 16 is reduced on shaping, and due to the fact that the opening 20 does not include any material that shall be pressed together on shaping, the shaping is not obstructed either.

Figure 2B:
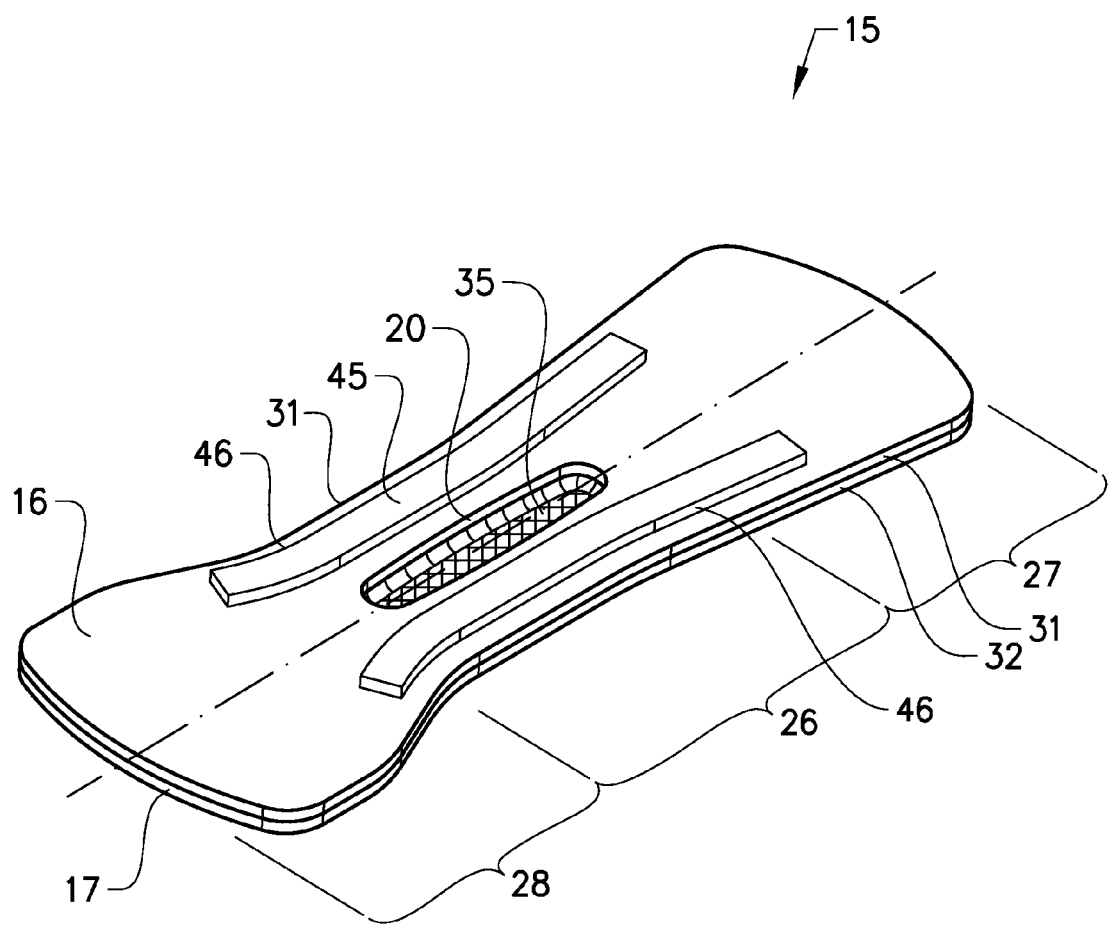
FIG. 2b shows the absorption body in FIG. 2 when a special two-piece acquisition material is arranged on the absorption body.

In FIG. 2*b* it is shown how a two-piece special acquisition material 45 is arranged on the side of the absorption body 15 that is intended to face towards the user upon use of an absorbent article comprising the absorption body 15.

The two parts of the acquisition material 45 are substantially elongated and arranged in the crotch area 26 of the absorption body 15, but can also extend out into the front and rear end area 27, 28 respectively of the absorption body 15.

Each respective part of the two parts of the acquisition material 45 is is arranged in a transverse direction between the centre line 25 and the longitudinal edges 31, 32 of the absorption body 15, wherein the respective part of the edges 46 of the acquisition material 45 that are arranged outermost in a transverse direction are arranged at a distance of 10-30 mm, preferably 15-30 mm from the longitudinal edges 31, 32 of the absorption body 15.

Alternatively, the acquisition material 45 can consist of a material having a larger central opening, the longitudinal outer edges of the acquisition material 45 being arranged at the same distance from the longitudinal edges 31, 32 of the absorption body 15 as defined for the two-piece acquisition material 45 above.

The acquisition material 45 has larger pores than the first absorption layer 16 against which the acquisition material 45 rests. For example, the acquisition material 45 consists of synthetic fibres of polyethylene, polypropylene or polyester. Also so-called two-component fibres comprising at least one of the fibre qualities polyethylene, polypropylene or polyester. The task of the acquisition material 45 is to take up and temporarily store fluid that impacts on the article at a high flow rate, in order thereafter to be drained by the absorption body 15 at a slower rate.

Figure 3A:
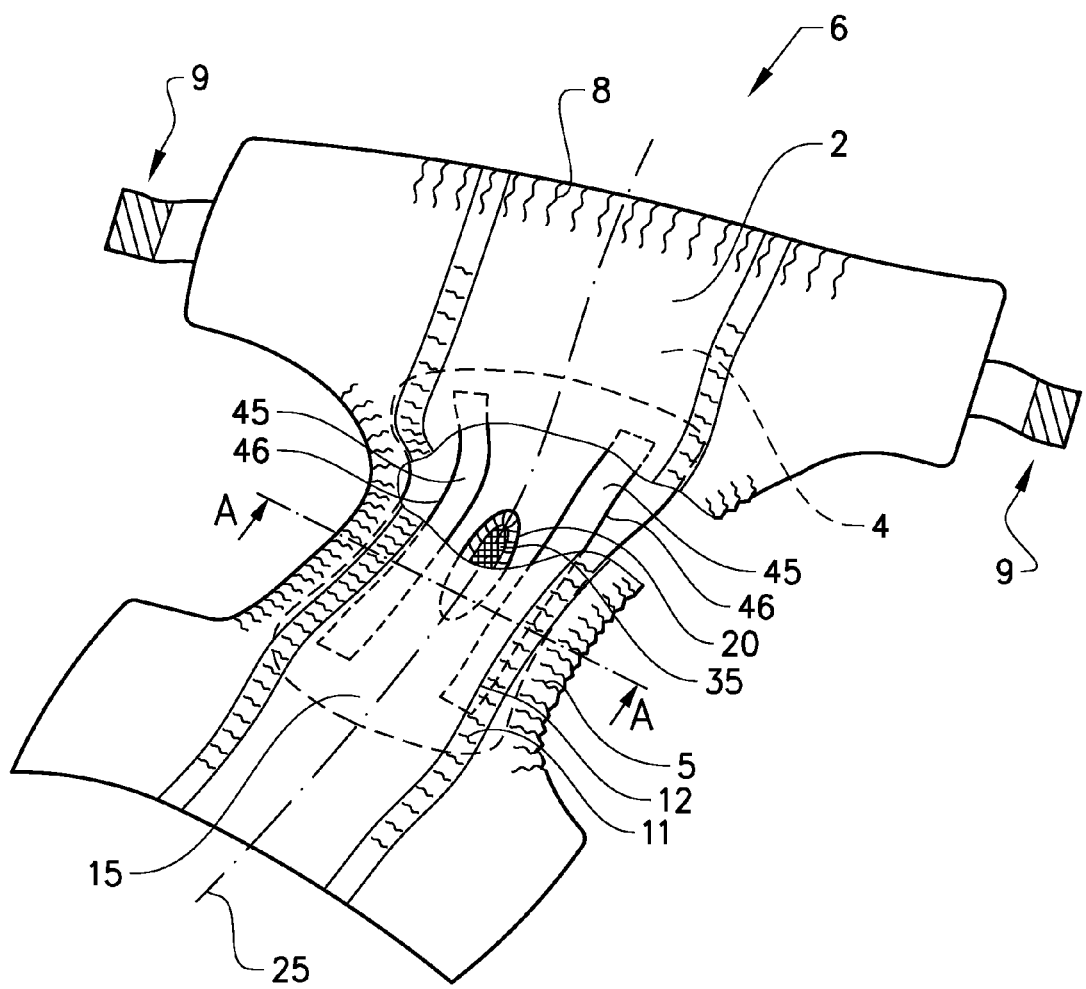
FIG. 3a shows an absorbent article intended for urine absorption comprising an absorption body in accordance with FIGS. 1 and 2.

FIG. 3*a* shows an absorbent article 6 comprising an absorption body 15 in accordance with a first aspect of the present disclosure.

The article 6 can consist of a baby diaper or an incontinence pad intended for incontinent adult users.

The absorbent article 6 shown in FIG. 3*a* is a so-called all-in-one diaper, but the bowl shaping specific to the present disclosure is also relevant for alternative articles intended for urine absorption, such as pant diapers and belt diapers, for example.

The article 6 comprises a liquid-permeable envelope layer 2, arranged over the surface of the article that is intended upon use to face towards the user and a rear layer 4 arranged over the surface of the article 6 that is intended upon use to face away from the user.

Arranged between the liquid-permeable envelope layer 2 and the rear layer 4 is an absorption body 15 in accordance with the first aspect of the present disclosure. The absorption body 15 is described in connection with FIGS. 1, 2 and 2*b* above.

To better clarify how the article 6 is built up under the liquid-permeable envelope layer 2, an area of this has been opened up. In the area that has been opened up, there can be seen, from top to bottom through the article 6, the two-piece acquisition material 45, the absorption body 15, the longitudinal opening 20 of the first absorption layer 16 and the longitudinal compression 35 of the second absorption layer 17.

The liquid-permeable envelope layer 2 extends outside the absorption body 15 along the entire circumference of the absorption body 15. The envelope layer 2 can consist of any material suitable for the purpose. Examples of commonly occurring liquid-permeable envelope materials are nonwoven material, perforated plastic films, mesh of plastic or textile, and liquid-permeable foam layers.

In the areas between the edges 46 of the two-piece acquisition material 45 arranged outermost in the transverse direction and the longitudinal edges 31, 32 of the absorption body 15, the liquid-permeable envelope layer 2 has hydrophilic properties. The hydrophilic properties in these two edge areas mean that fluid that runs on top of the liquid-permeable envelope layer 2 is intercepted with a certain increased probability and transported into the absorption body 15. Hydrophilic properties can be obtained, for example, by treating the liquid-permeable envelope layer 2 with surface-active substances.

The rear layer 4 also extends outside the absorption body 15 along its entire circumference. Normally occurring rear layers are usually liquid-impermeable, consisting of a thin liquid-impermeable plastic film.

The rear layer 4 that consists of a liquid-impermeable yet vapour-permeable material is now generally standard in many types of absorbent articles. The vapour permeability means that the article is breathable, which makes the article considerably more comfortable to use.

Rear layers consisting of a laminate comprising a liquid-impermeable material acting as a liquid barrier and a textile-like material for making the article garment-like on the outwardly oriented surface of the article are also more or less to be regarded as standard nowadays.

The liquid-permeable envelope layer 2 and rear layer 4 are joined to one another outside the entire circumference of the absorption body 15.

The absorbent article 6 has leg elastic 5. The leg elastic 5 extends in a longitudinal direction between the longitudinal edges of the absorption body 15 and the longitudinal edges of the article 6. The leg elastic is intended to seal against the user's thighs and thereby prevent fluid from running out over the edge of the article.

The leg elastic 5 comprises three elastic elements arranged between the liquid-permeable envelope layer 2 and rear layer 4, but can in alternative articles comprise more or fewer elastic elements.

To further prevent fluid or faeces from leaking out over the edges of the absorbent article, the article is provided with inner lateral leakage barriers 11, so-called standing gathers. The inner lateral leakage barriers 11 are arranged lying close to the longitudinal edges of the absorption body 15. The respective inner lateral leakage barriers 11 comprise, adjacent to their free edge, an elastic element 12 connected to the lateral leakage barrier 11 in a prestressed state. The elastic elements can consist of one or more elastic threads, elastic ribbon, elastic film, elastic foam or alternative.

The inner lateral leakage barriers 11 consist of separate singly folded material strips, the limbs of the strips being connected to the liquid-permeable envelope layer 2. Alternatively, the lateral leakage barriers 11 can consist of pleats in the liquid-permeable envelope layer 2.

When the prestressed elastic elements 12 are released, they contract together with the free edges of the inner lateral leakage barriers 11, wherein the inner lateral leakage barriers 11 are brought into a raised configuration away from the liquid-permeable envelope layer 2, at least in the crotch part of the article 6.

The back part of the absorbent article 6 is provided with so-called waist elastic 8, which consists of elastic elements arranged along the rear transverse edge of the article 6. The waist elastic 8 is intended to give the absorbent article 6 a soft and flexible encircling around the user's waist. In the article described, only the back part is provided with waist elastic 8. In alternative articles the front part can also be provided with waist elastic.

In the rear part of the absorbent article 6, are special fastening elements 9 intended to be joined to the front part when putting the article on a user arranged.

Figure 3B:
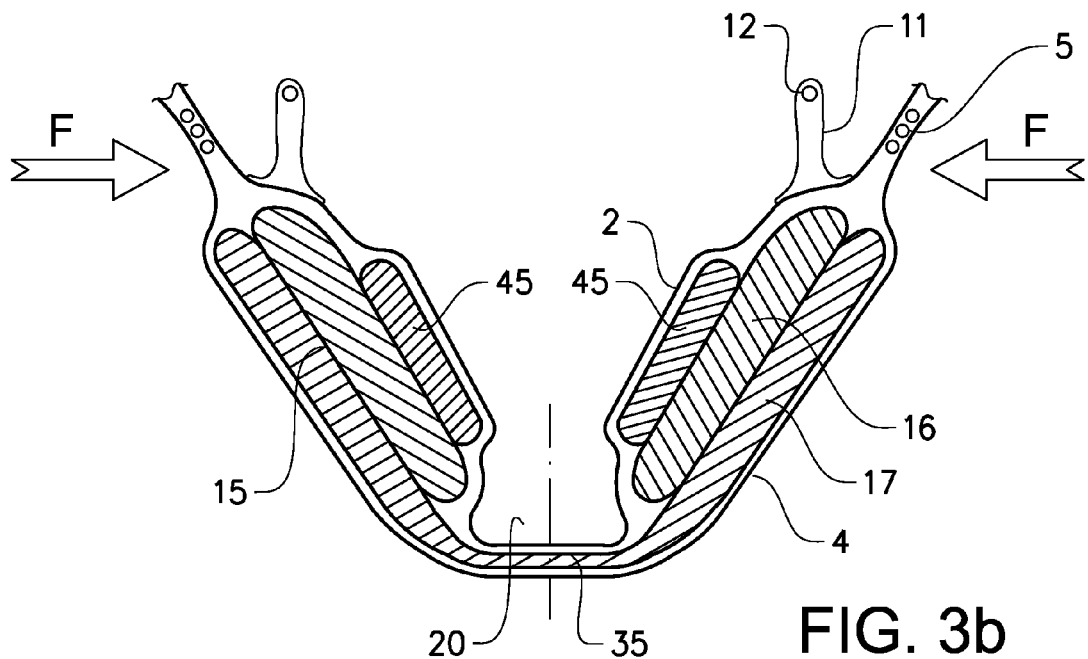
FIG. 3b shows how the cross section A-A in FIG. 3a is shaped upon use when the article is exposed to lateral forces perpendicular to the longitudinal direction from a user's thighs.

FIG. 3b shows how the cross section A-A in FIG. 3a is shaped when the article 6 is exposed to lateral forces (F) from a user's thighs when in use.

The absorption body 15 that is described in connection with FIGS. 1 and 2 above is arranged between the article's liquid-permeable envelope layer 2 and the rear layer 4.

The absorption body 15 is arranged with the first absorption layer 16 oriented towards the user and the second absorption layer 17 oriented away from the user when in use.

The two-piece acquisition material 45 is arranged between the first absorption layer 16 and the liquid-permeable envelope layer 2.

The inner lateral barriers 11 are arranged close to the longitudinal edges of the absorption body 15.

The figure shows how the bowl shape is formed by the absorption body 15 shaping itself around the longitudinal compression 35 of the second absorption layer 17, which compression forms an effective fold notch. The opening 20 of the first absorption layer 16 is reduced in width at the same time when the absorption body 15 is folded/shaped, and due to the fact that the opening 20 does not comprise any material that must be pressed together, no resistance arises upon folding/shaping.

The bowl shape means that urine that cannot be absorbed by the absorption body 15 at the rate that the urine is supplied can be stored temporarily in the bowl shape created.

Figure 3C:
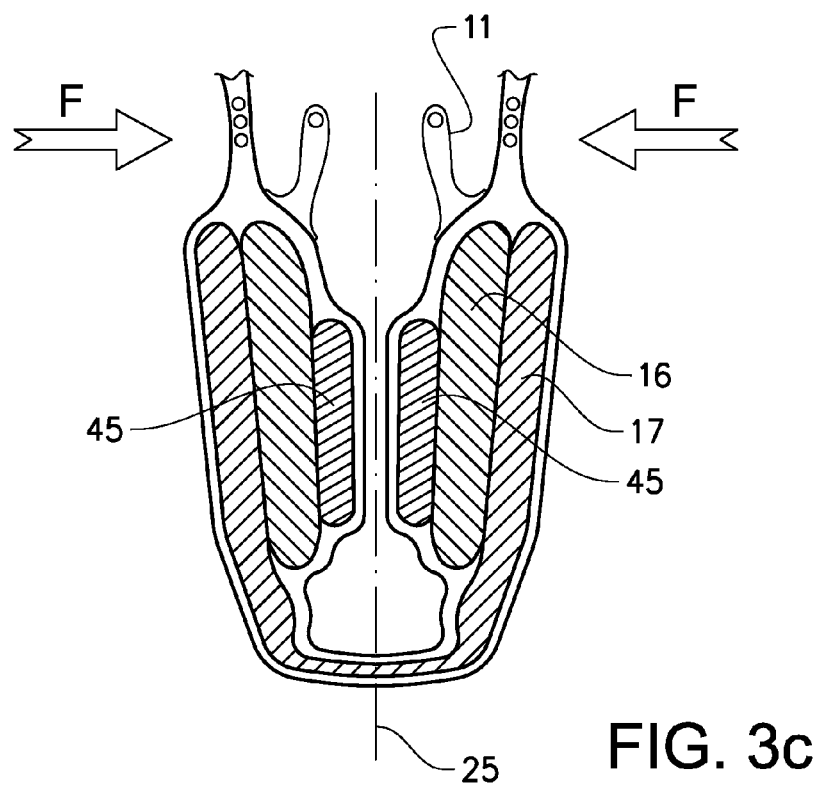
FIG. 3c shows how the cross section A-A in FIG. 3a can be shaped upon use when the article is exposed to lateral forces perpendicular to the longitudinal direction from a user's thighs when the distance between the user's thighs is small.

FIG. 3c shows how the cross section A-A in FIG. 3a can be shaped upon use when the article is exposed to lateral forces perpendicular to the longitudinal direction from a user's thighs when the distance between the thighs is small.

The crotch area of the article has been compressed thereby so much in a transverse direction that one part of the two-piece acquisition material 45 arranged on one side of the centre line 25 virtually rests against the other part of the two-piece acquisition material 45 arranged on the opposite side of the centre line. In extreme cases it occurs that both parts of the two-piece acquisition material 45 rest against one another.

Figure 4A:
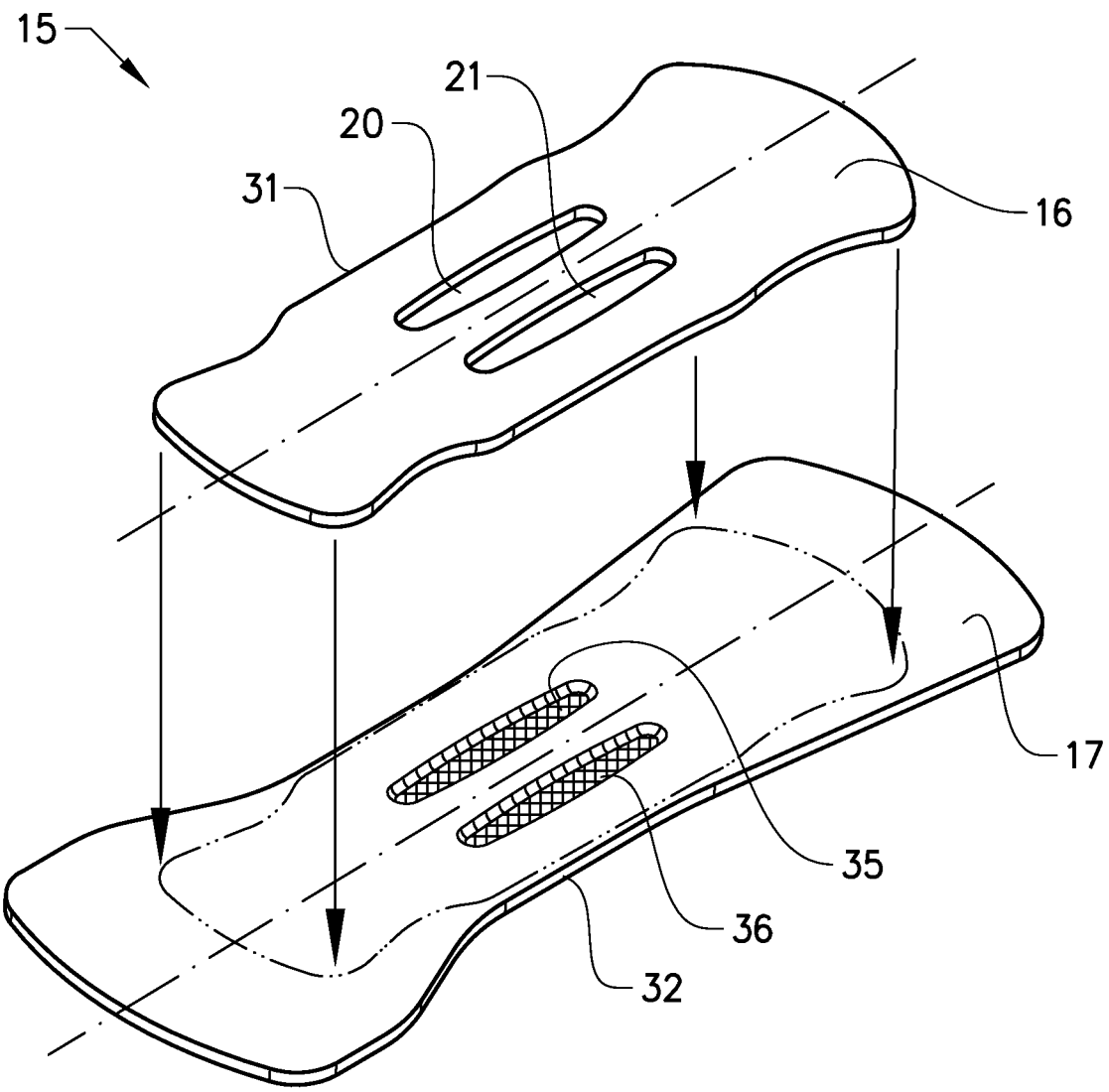
FIG. 4a shows a drawing in perspective of an absorption body in accordance with an alternative aspect of the present disclosure, in which the two absorption layers of the absorption body are shown separated from one another for greater clarity.
Figure 4B:
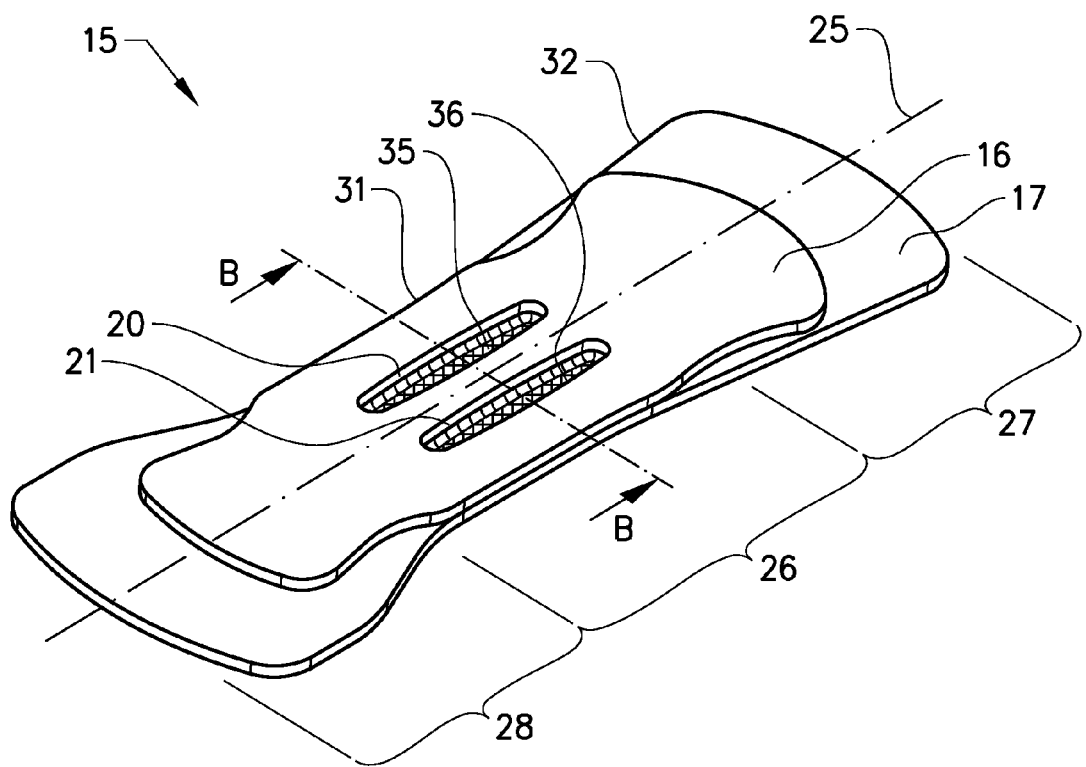
FIG. 4b shows the absorption body in FIG. 4a when the two absorption layers of the absorption body are arranged on one another.

FIGS. 4a and 4b show an absorption body 15 in accordance with an alternative aspect of the present disclosure. The absorption body 15 comprises a first absorption layer 16 and a second absorption layer 17 comprising at least cellulose fluff pulp.

In FIG. 4a, the first and second absorption layer 16, 17 of the absorption body 15 have been separated from one another to increase clarity, while FIG. 4b shows the absorption body 15 as it is arranged when it is applied to an absorbent article.

The absorption body 15 has a front end area 27, a rear end area 28 and a crotch area 26 arranged between the end areas 27, 28 as well as a longitudinal centre line 25.

The first absorption layer 16 has longitudinal edges 31.

Furthermore, the first absorption layer 16 has a first longitudinal opening 20 and a second longitudinal opening 21.

The openings 20, 21 have their main extensions in the longitudinal direction in the crotch area 26, but can also extend into both the front and rear end area 27, 28.

Transversely the openings 20, 21 are arranged on each side of the centre line 25, between said centre line 25 and the respective longitudinal edge 31.

The openings 20, 21 extend in a longitudinal direction 30% of the length of the first absorption layer 16, but in alternative aspects of the present disclosure they can have an extension in a longitudinal direction of between 10% and 100% of the length of the first absorption layer 16.

Perpendicular to the longitudinal direction, the openings have a width of 15 mm, but in alternative aspects of the present disclosure they can vary between 2 and 30 mm, preferably between 5 and 20 mm and even more preferably between 8 and 15 mm.

The second absorption layer 17 has longitudinal edges 32.

Furthermore, the second absorption layer 17 has a first longitudinal compression 35 and a second longitudinal compression 36. The compressions 35, 36 have their main extensions in a longitudinal direction in the crotch area 26, but can also extend into both the front and rear end area 27, 28. Transversely the compressions 35, 36 are arranged on each side of is the centre line 25, between said centre line 25 and the respective longitudinal edge 32.

The compressions 35, 36 extend in a longitudinal direction 30% of the length of the second absorption layer 17, which means that the compressions 35, 36 extend as far as the openings 20, 21 in the first absorption layer 16.

In alternative aspects of the present disclosure, the compressions 35, 36 can have an extension in a longitudinal direction from 30% of the length of the openings 20, 21 of the first absorption layer 16 up to the entire length of the second absorption layer 17.

The compressions 35, 36 have a width perpendicular to the longitudinal direction of 15 mm, but in alternative aspects of the present disclosure can have a width of between 2 and 30 mm, preferably between 5 and 20 mm and even more preferably between 8 and 15 mm.

The compressions 35, 36 are clearly visible in relation to surrounding parts of the absorption layer 17, the thickness of the absorption layer 17 having been reduced by 20-90% in the central parts of the compression 17, preferably by 50-90% and even more preferably by 70-90%.

The absorption body 15 is distinguished primarily in that the first opening 20 arranged in the first absorption layer 16 substantially overlaps the first compression 35 arranged in the second absorption layer 17 and that the second opening 21 arranged in the first absorption layer 16 substantially overlaps the second compression 36 arranged in the second absorption layer 17.

The crotch area 26 of the absorption body 15 is shaped, when it is exposed to forces substantially perpendicular to the longitudinal centre line 25, like a U with the first absorption layer 16, comprising the openings 20, 21, oriented inwards in the U-shape. The second absorption layer 17, comprising the is compressions 35, 36, is oriented in this case outwards on the U-shape.

In the same way as described above in connection with FIGS. 1 and 2, the combination of overlapping opening—compression functions for the absorption body 15 according to this aspect of the present disclosure, i.e. the compressions act like fold notches that are not obstructed by any material from being pressed together in the openings.

Figure 4C:
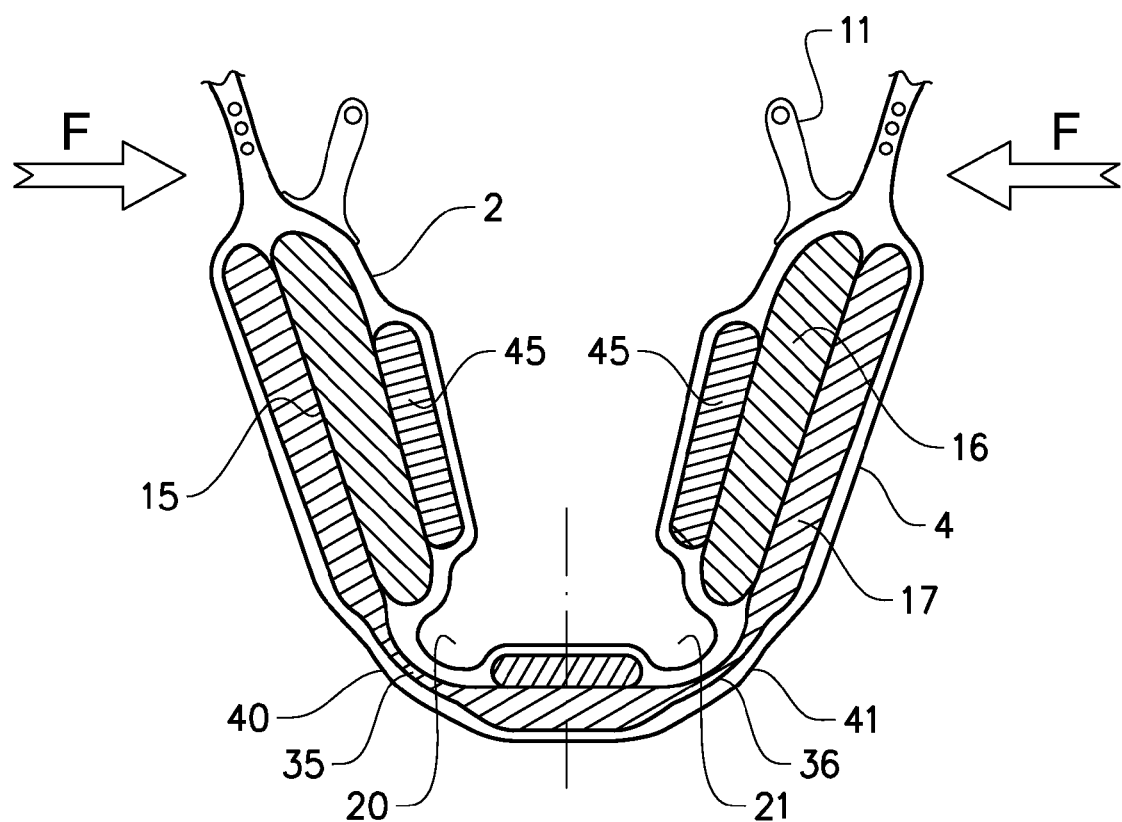
FIG. 4c shows how the cross section B-B in FIG. 4b is shaped upon use when the absorption body in FIG. 4b is arranged in an absorbent article that is exposed to lateral forces perpendicular to the longitudinal direction from a user's thighs.

FIG. 4c shows how the cross section B-B in FIG. 4b is shaped when the absorption body 15 is arranged between a liquid-permeable envelope layer 2 and a liquid-impermeable rear layer 4 in an absorbent article and when the article is exposed to lateral forces (F) from a user's thighs when in use.

The absorbent article is preferably intended for urine absorption and can be a baby diaper, for example, or an incontinence article intended for adult users.

The absorption body 15 as described in connection with FIGS. 4a and 4b above is arranged between the article's liquid-permeable envelope layer 2 and rear layer 4.

The absorption body 15 is arranged with the second absorption layer 17 oriented away from the user and the first absorption layer 16 oriented towards the user when in use.

The longitudinal compressions 35, 36 of the second absorption layer 17 cooperate with the longitudinal openings 20, 21 of the first absorption layer 16 and form two outwardly oriented side pleats 40, 41 of the U-shape.

The two-piece acquisition material 45 is arranged between the first absorption layer 16 and the liquid-permeable envelope layer 2 and the inner lateral barriers 11 are arranged close to the longitudinal edges of the absorption body 15.

The two outwardly oriented lateral pleats 40, 41 are shaped around the respective compression 35, 36 of the second absorption layer 17, which form effective fold notches. The two longitudinal openings 20, 21 of the first absorption layer 16 reduce in width when the lateral pleats 40, 41 are folded/shaped and due to the fact that the openings 20, 21 do not comprise any material, no resistance arises upon folding/shaping.

Figure 5:
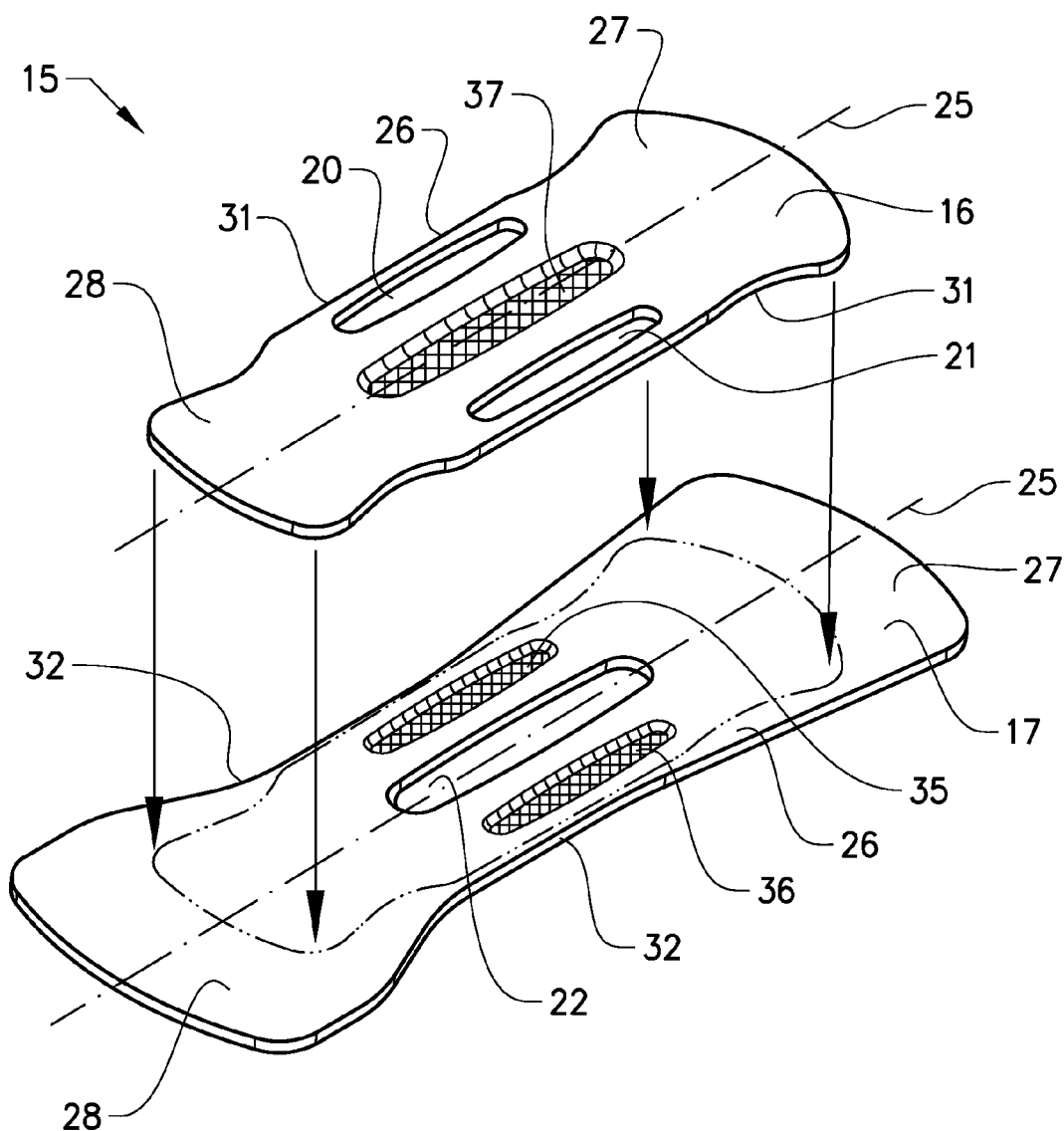
FIG. 5 shows a drawing in perspective of an absorption body in accordance with a third aspect of the present disclosure, in which the two absorption layers of the absorption body are shown separated from one another for greater clarity.
Figure 6:
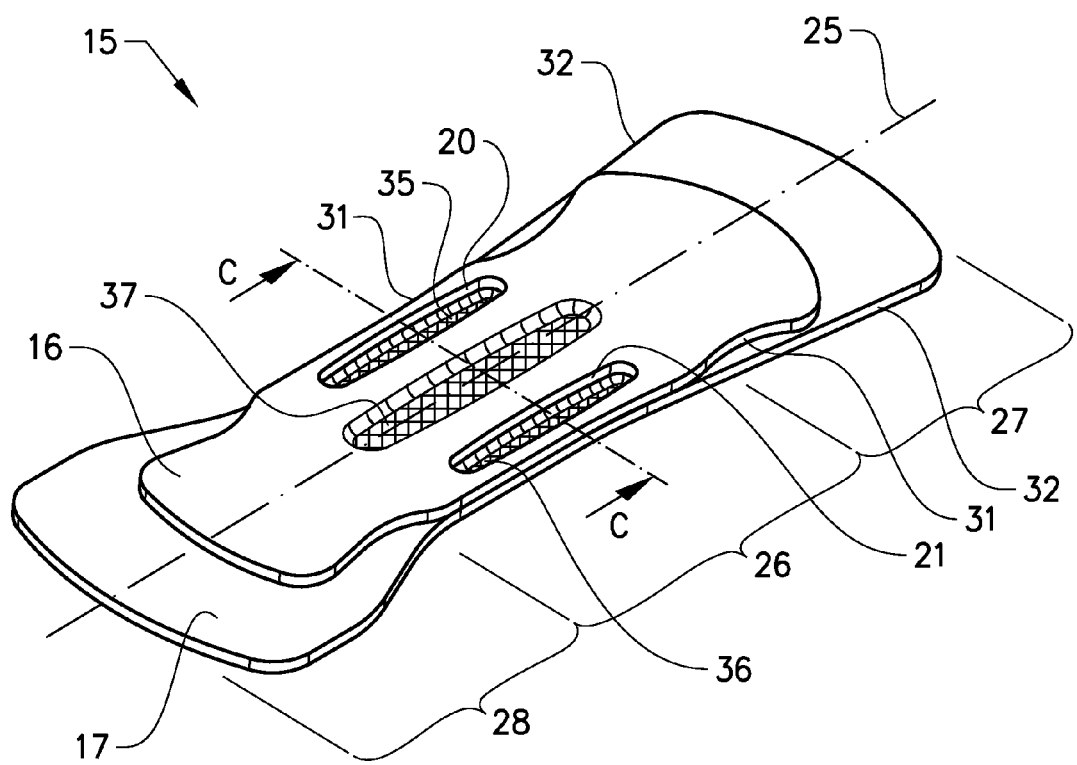
FIG. 6 shows the absorption body in FIG. 5 when the two absorption layers of the absorption body are arranged on one another.

FIGS. 5 and 6 show an absorption body 15 in accordance with a further aspect of the present disclosure. The absorption body 15 is substantially built up in the same way as the absorption body described in connection with FIGS. 4a and 4b above, but with the additions that the first absorption layer 16 has a third longitudinal compression 37 and the second absorption layer 17 has a third longitudinal opening 22.

In FIG. 5, the first and second absorption layers 16, 17 of the absorption body 15 have been separated from one another to increase clarity, while FIG. 6 shows the absorption body 15 as it is arranged when it is applied in an absorbent article.

The third compression 37, coinciding with the centre line 25, has its main extension in the longitudinal direction in the crotch area 26, but can also extend into both the front and rear end area 27, 28.

The compression 37 extends in a longitudinal direction 30% of the length of the first absorption layer 16, but in alternative aspects of the present disclosure can have an extension in a longitudinal direction from 30% of the length of the opening 22 of the second absorption layer 17 up to the entire length of the first absorption layer 16.

The compression 37 further has a width perpendicular to the longitudinal direction of 15 mm but in alternative aspects of the present disclosure can have a width of between 2 and 30 mm, preferably between 5 and 20 mm and even more preferably between 8 and 15 mm.

The third longitudinal opening 22, coinciding with the centre line, has its main extension in a longitudinal direction in the crotch area 26, but can also extend into both the front and rear end area 27, 28.

The opening 22 extends 30% of the length of the second absorption layer 17 in a longitudinal direction, but in alternative aspects of the present disclosure is can have an extension in a longitudinal direction of between 10% and 100% of the length of the second absorption layer 17.

The opening has a width perpendicular to the longitudinal direction of 15 mm but can vary in alternative aspects of the present disclosure between 2 and 30 mm, preferably between 5 and 20 mm and even more preferably between 8 and 15 mm.

The absorption body 15 is distinguished primarily in that the third opening 22 arranged in the second absorption layer 17 and the third compression 37 arranged in the first absorption layer 16 substantially overlap one another and that the first opening 20 arranged in the first absorption layer 16 substantially overlaps the first compression 35 arranged in the second absorption layer 17 and that the second opening 21 arranged in the first absorption layer 16 substantially overlaps the second compression 36 arranged in the second absorption layer 17.

The crotch area 26 of the absorption body 15 is shaped, when it is exposed to forces substantially perpendicular to the longitudinal centre line 25, like a W with the first absorption layer 16, comprising the compression 37 and the openings 20, 21, oriented inwards in the W-shape. The second absorption layer 17, comprising the opening 22 and the compressions 35, 36, is oriented here on the outside of the W-shape.

Figure 7:
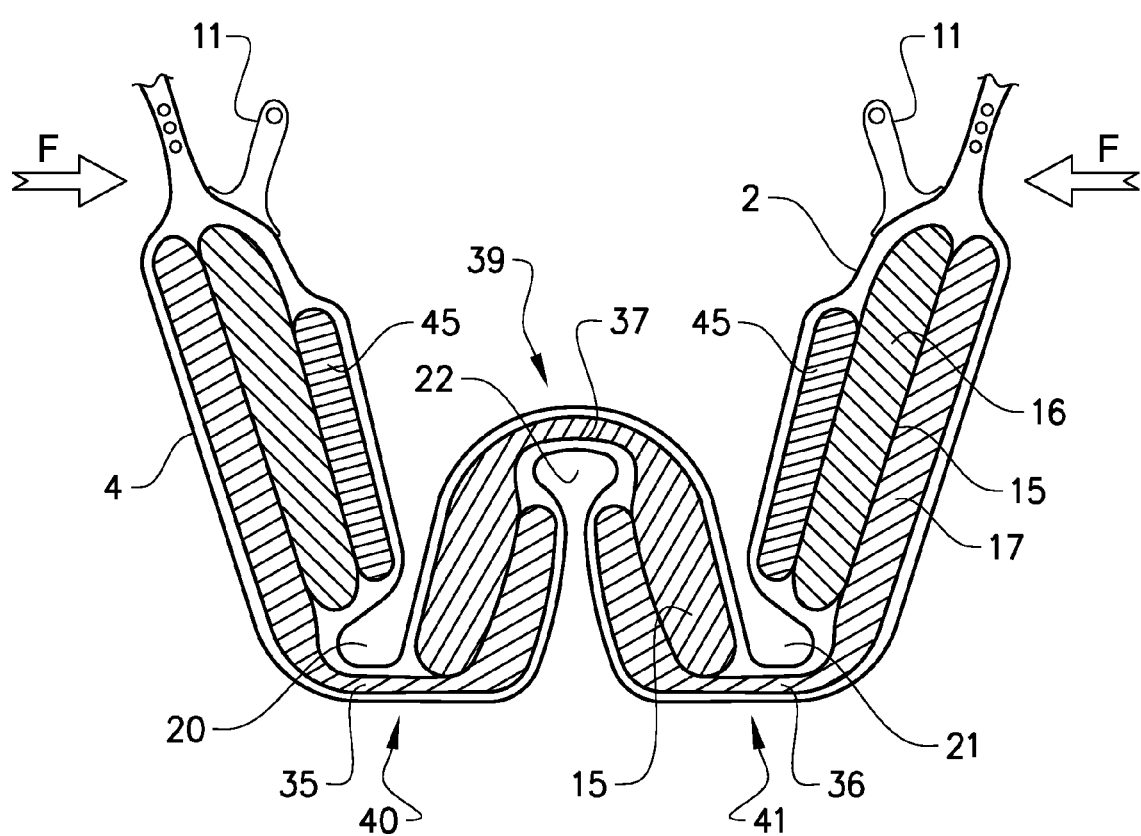
FIG. 7 shows how the cross section C-C in FIG. 6 is shaped when the absorption body in FIG. 6 is arranged in an absorbent article that is exposed to lateral forces perpendicular to the longitudinal direction from a user's thighs.

FIG. 7 shows how the cross section C-C in FIG. 6 is shaped when the absorption body 15 is arranged between a liquid-permeable envelope layer 2 and a liquid-impermeable rear layer 4 in an absorbent article and when the article is exposed to lateral forces (F) from a user's thighs when in use.

The absorption body 15 as described in connection with FIGS. 5 and 6 above is arranged between the article's liquid-permeable envelope layer 2 and rear layer 4.

The absorption body 15 is arranged with the second absorption layer 17 oriented away from the user and the first absorption layer 16 oriented towards the user when in use.

The longitudinal compressions 35, 36 of the second absorption layer 17 cooperate with the longitudinal openings 20, 21 of the first absorption layer 16 and form two outwardly oriented side pleats 40, 41 of the W-shape.

The two-piece acquisition material 45 is arranged between the first absorption layer 16 and the liquid-permeable envelope layer 2 and the inner lateral barriers 11 are arranged close to the longitudinal edges of the absorption body 15.

The two outwardly oriented lateral pleats 40, 41 are shaped in the same way as described above in connection with FIG. 4c.

The longitudinal third compression 37 of the first absorption layer 16 cooperates with the longitudinal opening 22 of the second absorption layer 17 and forms the inwardly oriented centre pleat 39 of the W-shape. The centre pleat 39 is shaped around the compression 37 of the first absorption layer 16, which compression forms an effective fold notch. The opening 22 of the second absorption layer reduces in width when the central pleat 39 is folded/shaped and due to the fact that the opening 22 does not comprise any material, no resistance arises upon folding/shaping.

The present disclosure also covers all conceivable combinations of the described aspects.

Furthermore, the present disclosure is not limited to the aforementioned aspects, but can naturally be used for other combinations within the scope of the following patent claims.

The invention claimed is:

1. Absorption body configured to form part of an absorbent disposable article having a longitudinal centre line, a crotch area, a front end area and a rear end area, wherein the absorption body comprises:
    a first absorption layer that is configured to face towards the user when in use and has longitudinal edges; and
    a second absorption layer that is configured to face away from the user when in use and has longitudinal edges, wherein
    the first absorption layer has a first longitudinal opening arranged in the crotch area,
    the second absorption layer has a first longitudinal compression arranged in the crotch area,
    the first longitudinal opening and the first longitudinal compression overlap one another, and
    the first longitudinal compression has a thickness that is 10% to 30% of a thickness of the second absorption layer, and a length of the first longitudinal compression is equal to or less than 30% of a length of the first absorption layer in a longitudinal direction.

2. The absorption body according to claim 1, wherein the first longitudinal opening and the first longitudinal compression substantially coincide with the longitudinal centre line.

3. The absorption body according to claim 1, wherein
    the first absorption layer has a second longitudinal opening arranged in the crotch area between the longitudinal centre line and one longitudinal edge of the first absorption layer,
    the first longitudinal opening is arranged between the longitudinal centre line and the one opposing longitudinal edge of the first absorption layer,
    the second absorption layer has a second longitudinal compression arranged in the crotch area between the longitudinal centre line and one longitudinal edge of the second absorption layer,
    the first longitudinal compression is arranged between the longitudinal centre line and an opposing longitudinal edge of the second absorption layer, and
    the second longitudinal opening and the second longitudinal compression substantially overlap one another.

4. The absorption body according to claim 3, wherein the first absorption layer has a third longitudinal compression arranged in the crotch area and substantially coinciding with the longitudinal centre line,
    the second absorption layer has a third longitudinal opening arranged in the crotch area and substantially coinciding with the longitudinal centre line, and
    the third longitudinal compression and the third longitudinal opening overlap one another.

5. The absorption body according to claim 1, wherein an acquisition material is arranged on a side of the first absorption layer that is configured to face towards the user.

6. The absorption body according to claim 5, wherein the acquisition material is divided into two separate parts, one part is arranged between the longitudinal centre line and one longitudinal edge of the first and second absorption layers and the other part is arranged between the longitudinal centre line and the other longitudinal edge of the first and second absorption layers, and each respective part is at a distance from the longitudinal centre line and from an adjacent longitudinal edge.

7. The absorption body according to claim 5, wherein the first and second absorption layers have a basis weight of between 50 g/m$^2$ and 1000 g/m$^2$.

8. The absorption body according to claim 1, wherein a basis weight of the first absorption layer and a basis weight of the second absorption layer are substantially the same.

9. The absorption body according to claim 1, wherein the first and second absorption layers have a content of absorbent polymer material of between 0% and 80%.

10. The absorption body according to claim 9, wherein the absorbent polymer material is superabsorbent polymer.

11. The absorption body according to claim 1, wherein one of the first and second absorption layers has a greater extension in a longitudinal direction than the other of the first and second absorption layers.

12. The absorption body according to claim 1, wherein the front end area and the rear end area of the absorption body have a greater extension in a transverse direction than the crotch area.

13. The absorption body according to claim 1, wherein the disposable article consists of a baby diaper.

14. The absorption body according to claim 13, wherein the absorbent disposable article comprises a liquid-permeable envelope layer, and the envelope layer has hydrophilic properties which are arranged at least in a longitudinal zone overlapping the longitudinal edges of the first and second absorption layers.

15. The absorption according to claim 1, wherein the disposable article consists of an incontinence pad for incontinent adult users.

16. The absorption body according to claim 15, wherein the absorbent disposable article comprises a liquid-permeable envelope layer, and the envelope layer has hydrophilic properties which are arranged at least in a longitudinal zone overlapping the longitudinal edges of the first and second absorption layers.

17. The absorption body according to claim 1, wherein an extension of the first absorption layer in a longitudinal direction is the same as the extension of the second absorption layer in the longitudinal direction.

18. The absorption body according to claim 1, wherein a length of the first longitudinal opening is only 30% of the length of the first absorption layer in a longitudinal direction.

* * * * *